US008969322B2

(12) United States Patent
Karumanchi

(10) Patent No.: US 8,969,322 B2
(45) Date of Patent: Mar. 3, 2015

(54) EXTRACORPOREAL DEVICES AND METHODS OF TREATING COMPLICATIONS OF PREGNANCY

(75) Inventor: S. Ananth Karumanchi, Chestnut Hill, MA (US)

(73) Assignee: Beth Israel Deconess Medical Center, Inc., Boston, MA (US)

( * ) Notice: Subject to any disclaimer, the term of this patent is extended or adjusted under 35 U.S.C. 154(b) by 232 days.

(21) Appl. No.: 13/107,198

(22) Filed: May 13, 2011

(65) Prior Publication Data
US 2011/0280825 A1 Nov. 17, 2011

Related U.S. Application Data

(60) Provisional application No. 61/334,824, filed on May 14, 2010, provisional application No. 61/346,216, filed on May 19, 2010.

(51) Int. Cl.
*A61K 31/715* (2006.01)
*A61K 31/737* (2006.01)
*A61K 31/78* (2006.01)

(52) U.S. Cl.
CPC ............... *A61K 31/737* (2013.01); *A61K 31/78* (2013.01)
USPC .... 514/59; 424/133.1; 424/145.1; 424/78.31; 435/7.1

(58) Field of Classification Search
CPC ................... A61M 2202/20; G01N 2800/368; A61K 2039/505
See application file for complete search history.

(56) References Cited

U.S. PATENT DOCUMENTS

| | | |
|---|---|---|
| 4,994,161 A | 2/1991 | Laue et al. |
| 5,194,596 A | 3/1993 | Tischer et al. |
| 5,219,739 A | 6/1993 | Tischer et al. |
| 5,240,848 A | 8/1993 | Keck et al. |
| 5,332,671 A | 7/1994 | Ferrara et al. |
| 6,447,768 B1 | 9/2002 | van Zonneveld et al. |
| 7,335,362 B2 | 2/2008 | Karumanchi et al. |
| 7,407,659 B2 | 8/2008 | Karumanchi et al. |
| 7,435,419 B2 | 10/2008 | Karumanchi et al. |
| 7,740,849 B2 | 6/2010 | Karumanchi et al. |
| 7,846,433 B2 | 12/2010 | Karumanchi et al. |
| 7,947,449 B2 | 5/2011 | Karumanchi et al. |
| 2004/0115278 A1 | 6/2004 | Putz et al. |
| 2005/0265996 A1* | 12/2005 | Lentz .................... 424/141.1 |
| 2006/0067937 A1 | 3/2006 | Karumanchi et al. |
| 2006/0153835 A1 | 7/2006 | Smith et al. |
| 2006/0183175 A1 | 8/2006 | Buhimschi et al. |
| 2007/0104707 A1 | 5/2007 | Karumanchi et al. |
| 2009/0117588 A1 | 5/2009 | Karumanchi et al. |
| 2009/0286271 A1 | 11/2009 | Karumanchi et al. |
| 2011/0014197 A1 | 1/2011 | Karumanchi et al. |
| 2011/0243956 A1 | 10/2011 | Karumanchi et al. |

FOREIGN PATENT DOCUMENTS

| | | |
|---|---|---|
| CN | 101163970 A | 4/2008 |
| WO | WO-2004/008946 A2 | 1/2004 |
| WO | WO-2005/077007 A2 | 8/2005 |
| WO | WO-2006/034507 A2 | 3/2006 |
| WO | WO-2008/030283 A1 | 3/2008 |

OTHER PUBLICATIONS

Abalos et al, Antihypertensive drug therapy for mild to moderate hypertension during pregnancy (Review), The Cochrane Library, 2012, Issue 10, pp. 1-167, published online Jan. 21, 2009.*
Liposorber (Liposorber LA-15 System Facts, Kaneka Corporation, Mar. 2009).*
"Apheresis," Wikipedia.org, accessed May 10, 2010, http://en.wikipedia.org/wiki/Apheresis.
Barleon et al., "Mapping of the Sites for Ligand Binding and Receptor Dimerization at the Extracellular Domain of the Vascular Endothelial Growth Factor Receptor FLT-$_1$," *The Journal of Biological Chemistry* 272: 10382-10388 (1997).
Charnock-Jones et al., "Identification and localization of alternately spliced mRNAs for vascular endothelial growth factor in human uterus and estrogen regulation in endometrial carcinoma cell lines," *Biol. Reprod.* 48: 1120-1128 (1993).
Cheifetz et al., "Endoglin is a component of the transforming growth factor-β receptor system in human endothelial cells," *J. Biol. Chem.* 267: 19027-19030 (1992).
"Dali® Direct Adsorption of Lipoproteins," Fresenius Medical Care (2005).
Fonsatti et al., "Endoglin (CD105): a powerful therapeutic target on tumor-associated angiogenetic blood vessels," *Oncogene* 22: 6557-6563 (2003).
Fonsatti et al., "Emerging role of endoglin (CD105) as a marker of angiogenesis with clinical potential in human malignancies," *Curr. Cancer Drug Targets* 3: 427-432 (2003).
Kendall et al., "Inhibition of vascular endothelial cell growth factor activity by an endogenously encoded soluble receptor," *Proc. Natl. Acad. Sci. USA* 90: 10705-10709 (1993).
Klingel et al., "Differential Indication of Lipoprotein Apheresis During Pregnancy," *Therapeutic Apheresis and Dialysis* 7(3): 359-364 (2003).
"The Liposorber® Patient Guide," Liposorber®, Kaneka Medical Products (2009).
Neufeld et al., "Similarities and differences between the vascular endothelial growth factor (VEGF) splice variants," *Cancer Metastasis Rev.* 15: 153-158 (1996).
Tischer et al., "The human gene for vascular endothelial growth factor. Multiple protein forms are encoded through alternative exon splicing," *J. Biol. Chem.* 266: 11947-11954 (1991).

(Continued)

*Primary Examiner* — Michael G Hartley
*Assistant Examiner* — Nabila Ebrahim
(74) *Attorney, Agent, or Firm* — Clark & Elbing LLP; Kristina Bieker-Brady

(57) ABSTRACT

The invention features extracorporeal methods for the treatment of a subject having a pregnancy related hypertensive disorder, such as pre-eclampsia or eclampsia. The invention also features devices used for the extracorporeal treatment of subjects have a pregnancy related hypertensive disorder, such as pre-eclampsia or eclampsia.

25 Claims, No Drawings

(56) References Cited

OTHER PUBLICATIONS

Wang et al., "Heparin-mediated extracorporeal low density lipoprotein precipitation as a possible therapeutic approach in preeclampsia," *Transfusion and Apheresis Science* 35: 103-110 (2006).

Zhang and Bowes, "Birth-weight-for-gestational-age patterns by race, sex, and parity in the United States population," *Obstet. Gynecol.* 86: 200-208 (1995).

International Search Report and Written Opinion for PCT/US2011/036409 mailed Sep. 9, 2011.

Thadhani et al., "Pilot study of extracorporeal removal of soluble fms-like tyrosine kinase 1 in preeclampsia," Circulation. 124(8):940-50 (2011).

Yokoyama, "Low density lipoprotein-apheresis with dextran sulfate-cellulose: development of a selective chemical adsorption system of plasma components," Plasma Ther Transfus Technol. 9(1):27-8 (1988).

Supplementary European Search Report for European Patent Application No. 11781339.4, dated Aug. 30, 2013 (4 pages).

Written Opinion for European Patent Application No. 11781339.4, dated Sep. 16, 2013 (5 pages).

Examiner's Report for Australian Patent Application No. 2011252954, issued Feb. 20, 2014 (4 pages).

Office Action for Chinese Patent Appliation No. 201180022894.9, dated Oct. 25, 2013 (28 pages).

Rajakumar et al., "Transcriptionally Active Syncytial Aggregates in the Maternal Circulation May Contribute to Circulating Soluble Fms-Like Tyrosine Kinase 1 in Preeclampsia," Hypertension. 59(2):256-64 2012. Accessed from <http://hyper.ahajournals.org/> on Jan. 4, 2012.

\* cited by examiner

EXTRACORPOREAL DEVICES AND METHODS OF TREATING COMPLICATIONS OF PREGNANCY

CROSS-REFERENCE TO RELATED APPLICATIONS

This application claims the benefit of U.S. provisional application Nos. 61/334,824, filed on May 14, 2010, and 61/346,216, filed May 19, 2010, each of which is herein incorporated by reference.

FIELD OF THE INVENTION

In general, this invention relates to the extracorporeal treatment, and devices for the extracorporeal treatment, of subjects having a pregnancy related hypertensive disorder.

BACKGROUND OF THE INVENTION

Pre-eclampsia is a syndrome of hypertension, edema, and proteinuria that affects 5 to 10% of pregnancies and results in substantial maternal and fetal morbidity and mortality. Pre-eclampsia accounts for at least 200,000 maternal deaths worldwide per year. The symptoms of pre-eclampsia typically appear after the $20^{th}$ week of pregnancy and are usually detected by routine measuring of the woman's blood pressure and urine. However, these monitoring methods are ineffective for diagnosis of the syndrome at an early stage, which could reduce the risk to the subject or developing fetus, if an effective treatment were available.

Currently there are no known cures for pre-eclampsia. Pre-eclampsia can vary in severity from mild to life threatening. A mild form of pre-eclampsia can be treated with bed rest and frequent monitoring. For moderate to severe cases, hospitalization is recommended and blood pressure medication or anticonvulsant medications to prevent seizures are prescribed. If the condition becomes life threatening to the mother or the baby the pregnancy is terminated and the baby is delivered pre-term.

Several factors have been reported to have an association with fetal and placental development and, more specifically, with pre-eclampsia. They include vascular endothelial growth factor (VEGF), soluble Flt-1 receptor (sFlt-1), placental growth factor (PlGF), and soluble endoglin. VEGF is an endothelial cell-specific mitogen, an angiogenic inducer, and a mediator of vascular permeability. VEGF has also been shown to be important for glomerular capillary repair. VEGF binds as a homodimer to one of two homologous membrane-spanning tyrosine kinase receptors, the fms-like tyrosine kinase (Flt-1) and the kinase domain receptor (KDR), which are differentially expressed in endothelial cells obtained from many different tissues. Flt-1, but not KDR, is highly expressed by trophoblast cells which contribute to placental formation. PlGF is a VEGF family member that is also involved in placental development. PlGF is expressed by cytotrophoblasts and syncytiotrophoblasts and is capable of inducing proliferation, migration, and activation of endothelial cells. PlGF binds as a homodimer to the Flt-1 receptor, but not the KDR receptor. Both PlGF and VEGF contribute to the mitogenic activity and angiogenesis that are critical for the developing placenta.

Soluble Flt-1 (sFlt-1), which lacks the transmembrane and cytoplasmic domains of the receptor, binds to VEGF with a high affinity but does not stimulate mitogenesis of endothelial cells. Careful regulation of angiogenic and mitogenic signaling pathways is critical for maintaining appropriate proliferation, migration, and angiogenesis by trophoblast cells in the developing placenta.

There is a need for a safe and effective treatment for pregnancy related hypertensive disorders, including pre-eclampsia and eclampsia, desirably before the onset of the most severe symptoms.

SUMMARY OF THE INVENTION

The present invention is based on the discovery of extracorporeal methods for treating pregnancy related hypertensive disorders, including pre-eclampsia and eclampsia. The invention also features extracorporeal devices that are useful for the treatment of pregnancy-related hypertensive disorders.

We have previously discovered that levels of sFlt-1 are markedly elevated in placental tissue samples from pregnant women suffering from pregnancy complications associated with hypertension, including pre-eclampsia. (See for example, U.S. Pat. Nos. 7,335,362; 7,407,659; and 7,435,419 and PCT Publication Numbers WO 2004/008946 and WO 2005/077007, herein incorporated by reference). sFlt-1 is known to antagonize VEGF and PlGF by acting as a "physiologic sink" and, in pre-eclamptic or eclamptic women, sFlt-1 may be depleting the placenta of necessary amounts of these essential angiogenic and mitogenic factors. Excess sFlt-1 may also lead to pre-eclampsia or eclampsia by disrupting the endothelial cells that maintain the blood-brain barrier and/or endothelial cells lining the choroid plexus of the brain thus leading to cerebral edema and the seizures seen in eclampsia. Methods that counter the effects of excess sFlt-1, allowing for an increase in the essential angiogenic and mitogenic factors, are useful for the treatment of pregnancy related hypertensive disorders.

We have surprisingly discovered that extracorporeal apheresis methods previously used effectively for removal of a positively charged protein from the blood, such as apolipoprotein, can be used to remove sFlt-1 from the blood of a pregnant woman suffering from pregnancy complications associated with hypertension, including pre-eclampsia.

Accordingly, in one aspect, the invention features a method of treating or ameliorating at least one symptom of a pregnancy related hypertensive disorder in a pregnant subject (e.g., a pregnant subject having elevated sFlt-1) which includes the step of extracorporeally removing sFlt-1 from the pregnant subject using an apheresis procedure, wherein the apheresis procedure includes the use of an agent (e.g., negatively charged polymer or polysaccharide) that binds to positively charged proteins (e.g., lipoprotein, apolipoprotein, fibrinogen, globulin, and C reactive protein), and wherein the apheresis procedure is sufficient to treat or ameliorate at least one symptom of the pregnancy related hypertensive disorder.

In another aspect, the invention features a method for reducing the level of sFlt-1 in a bodily fluid of a subject that includes the step of extracorporeally removing sFlt-1 from the pregnant subject using an apheresis procedure, wherein the apheresis procedure includes an agent that binds to positively charged proteins (e.g., lipoprotein, apolipoprotein, fibrinogen, globulin, and C reactive protein), and wherein the apheresis procedure is sufficient to reduce the level of sFlt-1 in a subject in need thereof.

In another aspect, the invention features an agent that binds positively charged proteins for use in a method for the treatment of a pregnancy related hypertensive disorder in a pregnant subject, wherein the agent is bound to an extracorporeal device and wherein the method includes an apheresis procedure that includes apheresis of a bodily fluid with the help of the extracorporeal device and wherein the apheresis results in the removal of sFlt-1 from the bodily fluid. In various embodiments, the agent includes dextran sulfate or anionic polyacrylate. In certain embodiments, the agent that binds to positively charged proteins does not include heparin. In additional embodiments, the pregnant subject has an increase in the sFlt-1 level as compared to a normal reference, standard, or level and the agent includes heparin. In various embodiments, the apheresis procedure includes drawing the pregnant subject's blood and directing the blood through an extracorporeal circuit that includes the agent.

In another aspect, the invention features an in vitro method for the removal of sFlt-1 from a bodily fluid from a pregnant subject having a pregnancy related hypertensive disorder, wherein the method includes the apheresing of the bodily fluid using an extracorporeal device having the agent bound thereto and wherein the apheresing results in the removal of sFlt-1 from the body fluid. In various embodiments, the agent includes dextran sulfate or anionic polyacrylate. In certain embodiments, the agent that binds to positively charged proteins does not include heparin. In additional embodiments, the pregnant subject has an increase in the sFlt-1 level as compared to a normal reference, standard, or level and the agent includes heparin. In various embodiments, the apheresis procedure includes drawing the pregnant subject's blood and directing the blood through an extracorporeal circuit that includes the agent.

In another aspect, the invention features the use of an autologous bodily fluid from which sFlt-1 has been reduced ex vivo in the manufacture of a medicament for treating a pregnancy related hypertensive disorder in a pregnant subject. In one embodiment, the sFlt-1 has been reduced by an apheresis procedure, wherein the apheresis procedure includes the use of an agent that binds to positively charged proteins. In various embodiments, the agent includes dextran sulfate or anionic polyacrylate. In certain embodiments, the agent that binds to positively charged proteins does not include heparin. In additional embodiments, the pregnant subject has an increase in the sFlt-1 level as compared to a normal reference, standard, or level and the agent is heparin. In various embodiments, the apheresis procedure includes drawing the pregnant subject's blood and directing the blood through an extracorporeal circuit that includes the agent. In additional embodiments, the autologous bodily fluid is a pregnant subject's blood and the sFlt-1 is removed by directing the blood through an extracorporeal circuit that includes the agent that binds positively charged proteins.

In various embodiments of each of the above aspects, the agent includes dextran sulfate or anionic polyacrylate, or does not include heparin.

In certain embodiments of the above aspects, the pregnant subject has an increase in the sFlt-1 level as compared to a normal reference, standard, or level and the agent includes heparin.

In one embodiment of each of the above aspects, the sFlt-1 level in the bodily fluid is reduced to 5 ng/ml or less. In another embodiment, the sFlt-1 level in the bodily fluid is reduced to 2 ng/ml or less. In another embodiment, the sFlt-1 level in the bodily fluid is reduced to 1 ng/ml or less.

In one embodiment of each of the above aspects, the apheresis procedure includes the step of drawing the pregnant subject's blood and directing the blood through an extracorporeal circuit that includes an agent that binds to positively charged proteins (e.g., lipoprotein, apolipoprotein, fibrinogen, globulin, and C reactive protein).

In various embodiments of each of the above aspects, the agent that binds to a positively charged protein includes a negatively charged polymer or a negatively charged polysaccharide (e.g., sulfonated polysaccharide, polystyrene sulfonic acid, and polyacrylic acid). In one example, the negatively charged polymer includes polystyrene sulfonic acid or polyacrylic acid. In another embodiment, the negatively charged polysaccharide includes sulfonated polysaccharide. Non-limiting examples include a polysaccharide that includes dextran sulfate, hyaluronic acid, chondroitin sulfate, keratin sulfate, or heparin sulfate, particularly wherein the pregnant subject has elevated sFlt-1 levels.

In various embodiments of each of the above aspects, the agent is immobilized with a water-insoluble porous carrier that includes a hydrophilic porous carrier (e.g., polysaccharide, hydrophilic polymer). Non-limiting examples of the polysaccharide include cellulose, pectin, chitin, agarose, carrageenan, and dextran. Non-limiting examples of the hydrophilic polymer include polyethylene glycol, polyvinyl alcohol, polyacrylic acid, and silica gel. In one embodiment, the water insoluble porous carrier includes cellulose or polyacrylic acid.

In various embodiments of each of the above aspects, the agent is packed in a cartridge includes the apheresis column. Non-limiting examples of apheresis columns that can be used in various embodiments of the invention include a LIPOSORBER column (dextran sulfate; Kaneka); a LIPOSORBER LA-15 column (dextran sulfate; Kaneka); a LIPOSORBER D column (dextran sulfate; Kaneka); a H.E.L.P column, a Therasorb column, or a DALI column (anionic polyacrylate; Fresenius SE). Desirably the apheresis column is a dextran sulfate or anionic polyacrylate based column.

In various embodiments of each of the above aspects, the apheresis procedure is done one time, two times, three time, four times, five times, six times, seven times, eight times, nine times, ten times, or as many times as needed during the pregnancy. Desirably, the apheresis procedure reduces sFlt-1 levels in the subject by at least 10%, 20%, 30%, 40%, 50%, 60%, 70%, 80%, 90% or more. In additional desirable embodiments, the apheresis procedure reduces sFlt-1 levels in the subject by greater than 61%. The reduction may be a total reduction after all apheresis procedures are complete or a reduction after a single apheresis procedure. In another embodiment of any of the above aspects, the apheresis procedure reduces the sFlt-1 levels in the subject to the sFlt-1 levels in a normal control or reference that is matched for gestational age. In another embodiment of any of the above aspects, the apheresis procedure reduces the sFlt-1 levels in the subject to within 20%, 10%, 5%, or 2% of the sFlt-1 levels in a normal control or reference that is matched for gestational age.

In additional embodiments of each of the above aspects, the pregnant subject has more than one symptom of a pregnancy related hypertensive disorder. Examples of symptoms of a pregnancy related hypertensive disorder are known in the art or described herein. The pregnant subject may have an increase in the sFlt-1 level or a decrease in the VEGF or PlGF protein levels as compared to a normal reference, standard, or level. In one embodiment, the pregnant subject has increased sFlt-1 levels relative to a normal reference, standard, or level. The normal reference may be a prior sample from the subject or a sample from a subject that does not have a pregnancy related hypertensive disorder. In one embodiment, the pregnant subject has an sFlt-1 level of at least 2 ng/ml or at least 5 ng/ml prior to the administering of the apheresis procedure.

In various embodiments of the invention, the pregnant subject is at least 17, 18, 19, 20, 21, 22, 23, 24, 25, 26, 27, 28, 29, 30, 31, 32, 33, 34, 35, 36, 37, 38, 39, or 40 weeks pregnant, in the second trimester of pregnancy, or in the third trimester of pregnancy. The subject may also be a post-partum subject. The pregnant subject may be diagnosed with or at risk of developing pregnancy related hypertensive disorder. Non-limiting examples of pregnancy related hypertensive disorders include pre-eclampsia, eclampsia, gestational hypertension, chronic hypertension, HELLP syndrome, and pregnancy with a small for gestational age (SGA) fetus. In one embodiment, the pregnancy related hypertensive disorder is pre-eclampsia or eclampsia.

In various embodiments of the invention, the method further includes monitoring the pregnancy related hypertensive disorder (e.g., pre-eclampsia or eclampsia) in the subject by measuring the level of sFlt-1, free VEGF, free PlGF, or soluble endoglin polypeptide in a bodily fluid sample from the subject.

In another embodiment of each of the above aspects, the level of sFlt-1 or soluble endoglin is measured and a decrease in the level of sFlt-1 or soluble endoglin after apheresis as compared to an sFlt-1 or soluble endoglin positive reference, standard, or level indicates an improvement in the pregnancy related hypertensive disorder in the subject. In one embodiment, the positive reference is from a sample from the same subject earlier in pregnancy or before apheresis.

In yet another embodiment of each of the above aspects, the level of free VEGF or free PlGF is measured and an increase in the level of free VEGF or free PlGF relative after apheresis as compared to a positive reference, standard, or level indicates an improvement in the pregnancy related hypertensive disorder in the subject. In one embodiment, the positive reference is from a sample from the same subject earlier in pregnancy or before apheresis.

In various embodiments, the monitoring is used to determine if the apheresis procedure should be repeated. In one example, a lack of decrease in sFlt-1 or soluble endoglin levels or a lack of increase in free VEGF or free PlGF levels after the apheresis procedure indicates the need for at least one additional apheresis procedure. In various embodiments, a lack of decrease or increase can mean no detectable decrease or increase, or a decrease or increase that is insufficient to provide therapeutic benefit.

In another embodiment of each of the above aspects, a level of sFlt-1 polypeptide less than 5 ng/ml, desirably less than 2 ng/ml, indicates an improvement in the pre-eclampsia or eclampsia. In another embodiment, the apheresis procedure is provided until the level of sFlt-1 in the subject is less than 2 ng/ml. In another embodiment, a decrease in the sFlt-1 level or an increase in the level of VEGF or PlGF polypeptide or nucleic acid measured during or after administering therapy relative to the value before therapy indicates an improvement in the pre-eclampsia or eclampsia.

In one embodiment of each of the above aspects, the method includes measuring the levels of sFlt-1 prior to the apheresis procedure and measuring the levels of sFlt-1 during or after the apheresis procedure, wherein the apheresis procedure is administered until the levels of sFlt-1 polypeptide are reduced by at least 10%, 20%, 30%, 40%, 50%, 60%, 70%, 80%, 90% or more during or after the apheresis procedure as compared to the sFlt-1 levels prior to the apheresis procedure. Desirably, the sFlt-1 levels are reduced by more than 61%.

In yet another embodiment, a metric or a ratio may be used to monitor the sFlt-1, VEGF, PlGF, or soluble endoglin levels before, during or after treatment. For example, a a pre-eclampsia anti-angiogenic index (PAAI): [sFlt-1/VEGF+PlGF] or sFlt-1/PlGF may be used to monitor the subject's progress during therapy. In one embodiment, a decrease in the PAAI value or sFlt-1/PlGF value as compared to a prior value measured in the same subject indicates an improvement in the pre-eclampsia or eclampsia. In additional embodiments, a PAAI value less than 20, more preferably less than 10 indicates an improvement in the pre-eclampsia or eclampsia. A decrease in the PAAI or sFlt-1/PlGF levels measured during or after therapy can also indicate an effective amount or duration of apheresis treatment. In one example, the apheresis procedure is carried out such that the PAAI is less than 20. In another example, the apheresis procedure is carried out such that the PAAI is less than 10. In another embodiment the apheresis procedure is carried out such that the sFlt-1/PlGF levels as measured, for example, on the Elecsys platform (Roche), are less than or equal to 80. In preferred embodiments, the measuring of the levels of sFlt-1, PlGF, or VEGF is done on two or more occasions and a change in the levels between measurements is used to monitor therapy or to determine appropriate duration or amount of apheresis treatment. In another example, the PAAI or sFlt-1/PlGF level after apheresis as compared to a positive reference, standard, or level indicates an improvement in the pregnancy related hypertensive disorder in the subject. In one embodiment, the positive reference is from a sample from the same subject earlier in pregnancy or before apheresis.

In preferred embodiments, the diagnostic and monitoring methods described herein are used to monitor the subject during therapy or to determine effective therapeutic dosages or to determine the number of treatments needed. In one embodiment, a decrease in the level of sFlt-1 polypeptide or nucleic acid measured during or after administering therapy relative to the value before therapy indicates an improvement in the pre-eclampsia or eclampsia. In such an embodiment, the clinician may decide to stop apheresis treatment. In another embodiment, a lack of decrease or an increase in the level of sFlt-1 polypeptide or nucleic acid measured during or after administering therapy relative to the value before therapy may indicate the need for continued apheresis treatment.

Any of the diagnostic methods known in the art or described herein (e.g., see for example, U.S. Pat. Nos. 7,335,362; 7,407,659; and 7,435,419; U.S. Patent Application Publication Numbers 2006/0067937 and 2007/0104707; and PCT Publication Numbers WO 2004/008946; WO 2005/077007; WO 2006/034507; and WO 2008/030283), can be used to monitor the pre-eclampsia or eclampsia in the subject before, during, or after treatment.

In various embodiments of all aspects of the invention, the method further includes administering an anticoagulation drug compound or an anti-hypertensive compound to the pregnant subject. Non-limiting examples of the anti-hypertensive compound include nicotine, theophylline, adenosine, nifedipine, minoxidil, and magnesium sulfate.

In various embodiments of all aspects of the invention, the bodily fluid is blood, serum, or plasma. In other embodiments of the above aspects, the subject is a pregnant human, a post-partum human, or a non-human (e.g., a cow, a horse, a sheep, a pig, a goat, a dog, or a cat). In one embodiment, the subject is a pregnant human having or at risk for developing a pregnancy related hypertensive disorder.

In various embodiments of each of the above aspects, the apheresis procedure includes the step of regenerating the apheresis column wherein the step of regenerating the apheresis column includes usage of eluent (e.g., an eluent that includes an inorganic salt solution). In one example, the apheresis cartridge that has been reduced the capacity during the treatment, is regenerated with eluent that includes 0.5-25 w/v % inorganic salt solution, or saline solution or 3-10 w/v % saline solution. In desired embodiments, 4-6 w/v % saline solution is used as eluent for the regeneration of the apheresis cartridge. The regeneration may occur during or after a treatment with the apheresis procedure.

In addition, the invention also features combinations of the methods described herein with any of the therapeutic, diagnostic, or monitoring methods described in U.S. Pat. Nos. 7,335,362; 7,407,659; and 7,435,419; U.S. Patent Application Publication Numbers 2006/0067937 and 2007/0104707; and PCT Publication Numbers WO 2004/008946; WO 2005/077007; WO 2006/034507; and WO 2008/030283, each of which is herein incorporated by reference.

For the purpose of the present invention, the following abbreviations and terms are defined below.

By "alteration" is meant a change (increase or decrease). An alteration can include a change in the expression levels of a gene or polypeptide as detected by standard art known methods such as those described below. As used herein, an alteration includes a 10% change in protein levels, preferably a 25% change, more preferably a 40%, 50%, 60%, 70%, 80%, 90% or greater change in expression levels.

By "apheresis," "hemapheresis," or "pheresis" is meant the process of removing a specific component from the blood, plasma, serum, or a fraction thereof, of a subject. Apheresis can be used to remove, separate, or collect one or more specific components of the blood, plasma, serum, or a fraction thereof. In general, apheresis includes the withdrawal of blood from the subject's body, removal of one or more components from the blood, and transfusion of the remaining blood back into the subject's body.

By "binding" is meant a non-covalent or a covalent interaction, preferably non-covalent, that holds two molecules together. Non-covalent interactions include, but are not limited to, hydrogen bonding, ionic interactions among charged groups, van der Waals interactions, and hydrophobic interactions among non-polar groups. One or more of these interactions can mediate the binding of two molecules to each other. Binding may exhibit discriminatory properties such as specificity or selectivity.

By "body mass index" is meant a number, derived by using height and weight measurements, that gives a general indication of whether or not weight falls within a healthy range. The formula generally used to determine the body mass index is a person's weight in kilograms divided by a person's height in meters squared or weight $(kg)/(height (m))^2$.

By "compound" is meant any small molecule chemical compound (peptidyl or non-peptidyl), antibody, nucleic acid molecule, polypeptide, or fragments thereof.

By "endoglin" or "Eng," also known as CD105, is meant a mammalian growth factor that has endoglin biological activity (see, for example, U.S. Patent Application Publication Nos. 20060067931 and 20070104707; WO2006034507; WO 2008/030283; Fonsatti et al., *Oncogene* 22:6557-6563, 2003; Fonsatti et al., *Curr. Cancer Drug Targets* 3:427-432, 2003; and Cheifetz et al., *J. Biol. Chem.* 267:19027-19030 (1992)) and is homologous to the protein defined by any of the following GenBank accession numbers: AAH29080 and NP_031958 (mouse); AAS67893 (rat); NP_000109, P17813, VSP_004233, CAA80673 (pig); and CAA50891, AAC63386, BT006872.1 or X72012.1 (human), or described in U.S. Pat. No. 6,562,957.

By "soluble endoglin polypeptide" or "sEng" is meant any circulating, non-membrane bound form of endoglin which includes at least a part of the extracellular portion of the endoglin protein and is substantially identical (e.g., 60%, 70%, 80%, 90%, 995%, 96%, 97%, 98%, 99%, or 100%) to the amino acid sequence encoding the extracellular portion of the endoglin protein (see, for example, U.S. Patent Application Publication Numbers 2006/0067937 and 2007/0104707; and PCT Publication Numbers WO 2006/034507 and WO 2008/030283).

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides or 10, 20, 30, 40, 50, 60, 70, 80, 90, 100, 150, 200, 250, 300, 350, 400, 450, 500, 550, 600, 640 amino acids or more.

By "gestational age" is meant a reference to the age of the fetus, counting from the first day of the mother's last menstrual period usually referred to in weeks.

By "gestational hypertension" is meant the development of high blood pressure without proteinuria after 20 weeks of pregnancy.

By a "history of pre-eclampsia or eclampsia" is meant a previous diagnosis of pre-eclampsia or eclampsia or pregnancy induced hypertension in the subject themselves or in a related family member.

By "intrauterine growth retardation (IUGR)" is meant a syndrome resulting in a birth weight which is less than the 10th percentile of the predicted fetal weight for the gestational age of the fetus. The current World Health Organization criterion for low birth weight is a weight less than 2,500 gm (5 lbs. 8 oz.) or below the $10^{th}$ percentile for gestational age according to U.S. tables of birth weight for gestational age by race, parity, and infant sex (Zhang and Bowes, *Obstet. Gynecol.* 86:200-208, 1995). These low birth weight babies are also referred to as "small for gestational age (SGA)". Pre-eclampsia is a condition known to be associated with IUGR or SGA.

By "pharmaceutically acceptable carrier" is meant a carrier that is physiologically acceptable to the treated mammal while retaining the therapeutic properties of the compound with which it is administered. One exemplary pharmaceutically acceptable carrier substance is physiological saline. Other physiologically acceptable carriers and their formulations are known to one skilled in the art and described, for example, in Remington's Pharmaceutical Sciences, ($20^{th}$ edition), ed. A. Gennaro, 2000, Lippincott, Williams & Wilkins, Philadelphia, Pa.

By "placental growth factor (PlGF)" is meant a mammalian growth factor that is homologous to the protein defined by GenBank accession number P49763, AAP35846, AAH01422 or NM 002632.4, or isoforms or fragments thereof, and that has PlGF biological activity. PlGF is expressed by cyto- and syncytiotrophoblasts in the placenta and PlGF biological activities include induction of proliferation, migration, and activation of endothelial cells, particularly trophoblast cells.

By "pregnancy related hypertensive disorder" is meant any condition or disease or pregnancy that is associated with or characterized by an increase in blood pressure. Included among these conditions are pre-eclampsia (including premature pre-eclampsia, severe pre-eclampsia), eclampsia, gestational hypertension, HELLP syndrome, (hemolysis, elevated liver enzymes, low platelets), abruption placenta, chronic hypertension, pregnancy with intra uterine growth restriction, and pregnancy with a small for gestational age (SGA) fetus. It should be noted that although pregnancy with a SGA fetus is not often associated with hypertension, it is included in this definition.

By "pre-eclampsia" is meant the multi-system disorder that is characterized by hypertension with proteinuria or edema, or both, glomerular dysfunction, brain edema, liver edema, or coagulation abnormalities due to pregnancy or the influence of a recent pregnancy. All forms of pre-eclampsia, such as premature, mild, moderate, and severe pre-eclampsia are included in this definition. Pre-eclampsia generally occurs after the 20$^{th}$ week of gestation. Pre-eclampsia is generally defined as some combination of the following symptoms: (1) a systolic blood pressure (BP)>140 mmHg and a diastolic BP>90 mmHg after 20 weeks gestation (generally measured on two occasions, 4-168 hours apart), (2) new onset proteinuria (1+ by dipstik on urinalysis, >300 mg of protein in a 24-hour urine collection, or a single random urine sample having a protein/creatinine ratio>0.3), and (3) resolution of hypertension and proteinuria by 12 weeks postpartum. Severe pre-eclampsia is generally defined as (1) a diastolic BP>110 mmHg (generally measured on two occasions, 4-168 hours apart) or (2) proteinuria characterized by a measurement of 3.5 grams or more protein in a 24-hour urine collection or two random urine specimens with at least 3+ protein by dipstick. In pre-eclampsia, hypertension and proteinuria generally occur within seven days of each other. In severe pre-eclampsia, severe hypertension, severe proteinuria and HELLP syndrome (hemolysis, elevated liver enzymes, low platelets) or eclampsia can occur simultaneously or only one symptom at a time. HELLP syndrome is characterized by evidence of thrombocytopenia (<100000 cells/µl), increased LDH (>600 IU/L) and increased AST (>70 IU/L). Occasionally, severe pre-eclampsia can lead to the development of seizures. This severe form of the syndrome is referred to as "eclampsia." Eclampsia can also include dysfunction or damage to several organs or tissues such as the liver (e.g., hepatocellular damage, periportal necrosis) and the central nervous system (e.g., cerebral edema and cerebral hemorrhage). The etiology of the seizures is thought to be secondary to the development of cerebral edema and focal spasm of small blood vessels in the kidney.

By "premature pre-eclampsia" is meant pre-eclampsia with onset of symptoms<37 weeks.

By "protein" or "polypeptide" or "polypeptide fragment" is meant any chain of more than two amino acids, regardless of post-translational modification (e.g., glycosylation or phosphorylation), constituting all or part of a naturally occurring polypeptide or peptide, or constituting a non-naturally occurring polypeptide or peptide.

By "control" or "reference" is meant any sample, standard, or level that is used for comparison purposes. For diagnostic or therapeutic monitoring purposes, a control sample may be a prior sample taken from the same subject (e.g., a sample from a prior time point or prior to the onset of symptoms). Non-limiting examples of control samples include: a sample from a pregnant subject or group of subjects not having a pregnancy related hypertensive disorder, such as pre-eclampsia or eclampsia; a subject or group of subjects that is pregnant but the sample was taken early in pregnancy (e.g., in the first or second trimester or before the detection of a pregnancy related hypertensive disorder, such as pre-eclampsia or eclampsia); a subject or group of subjects that is pregnant and has no history of a pregnancy-related hypertensive disorder, such as pre-eclampsia or eclampsia; a subject or group of subjects that is not pregnant; a sample of a purified reference polypeptide at a known normal concentration (i.e., not indicative of a pregnancy related hypertensive disorder, such as pre-eclampsia or eclampsia). Additional examples of control samples can be prepared from a subject or group of subjects prior to developing or diagnosis with a pregnancy-related hypertensive disorder. By "control standard or level" or "normal reference standard or level" is meant a value or number derived from a control sample. For example, a control standard or level can be a value or number derived from a normal subject or group of subjects that is matched to the sample subject, for example, by at least one of the following criteria: age, sex, weight, gestational age of the fetus, maternal age, maternal blood pressure prior to pregnancy, maternal blood pressure during pregnancy, BMI of the mother, weight of the fetus, prior diagnosis of pre-eclampsia or eclampsia, and a family history of pre-eclampsia or eclampsia. A "positive control" or "positive reference" sample, standard or value is a sample or value or number derived from a subject or group of subjects that is known to have a pregnancy-related hypertensive disorder. For example, a positive control sample may be from a subject or group of subjects having a pregnancy-related hypertensive disorder (e.g., pre-eclampsia or eclampsia), that is matched to the sample subject by at least one of the following criteria: gestational age of the fetus, maternal age, maternal blood pressure prior to pregnancy, maternal blood pressure during pregnancy, BMI of the mother, weight of the fetus, prior diagnosis of a pregnancy-related hypertensive disorder, and a family history of a pregnancy related hypertensive disorder. An "elevated sFlt-1 level" is an sFlt-1 level that is higher than a normal reference standard or level.

By "reduce or inhibit" is meant the ability to cause an overall decrease preferably of 10% or greater, more preferably of 20%, 30%, 40%, 50%, 60%, 70%, 80%, 90% or greater. As it relates to the reduction of the level of protein or nucleic acid, reduce is meant a decrease, preferably of 10% or greater, more preferably of 20%, 30%, 40%, 50%, 60%, 70%, 80%, 90% or greater, in the level of protein or nucleic acid as compared to an untreated sample. In one embodiment, the apheresis procedure will be carried out such that the level of sFlt-1 in the blood of a pregnant subject is reduced by at least 10%, 20%, 30%, 40%, 50% or more. The sFlt-1 levels can be measured before apheresis is administered and again during or after apheresis for comparison.

By "sample" is meant a bodily fluid (e.g., blood, serum, plasma, urine, saliva, amniotic fluid, or cerebrospinal fluid), tissue sample, cell or other specimen obtained from a subject. In one embodiment, the sample used for apheresis is a blood sample.

By "soluble Flt-1 (sFlt-1)" (also known as sVEGF-R1) is meant the soluble form of the Flt-1 receptor, that is homologous to the protein defined by GenBank accession number U01134, NM_001153392, NM_001159920, or EU368830 and that has sFlt-1 biological activity or isoforms or fragments thereof. The biological activity of an sFlt-1 polypeptide may be assayed using any standard method, for example, by assaying sFlt-1 binding to VEGF. sFlt-1 lacks the transmembrane domain and the cytoplasmic tyrosine kinase domain of the Flt-1 receptor. sFlt-1 can bind to VEGF and PlGF with high affinity, but it cannot induce proliferation or angiogenesis and is therefore functionally different from the Flt-1 and KDR receptors. sFlt-1 was initially purified from human umbilical endothelial cells and later shown to be produced by trophoblast cells in vivo. As used herein, sFlt-1 can include any sFlt-1 family member or isoform (e.g., alternatively spliced isoforms). sFlt-1 can also mean degradation products or fragments that result from enzymatic cleavage of the Flt-1 receptor and that maintain sFlt-1 biological activity.

By "specifically binds" is meant a compound which recognizes and binds a polypeptide of the invention but that does not substantially recognize and bind other molecules in a sample, for example, a biological sample, which naturally includes a polypeptide of the invention.

By "specific removal" or "selective removal" is meant the removal of one polypeptide or component (e.g., using apheresis) without substantial removal of another polypeptide or component of a sample (e.g., blood).

By "subject" is meant a mammal, including, but not limited to, a human or non-human mammal, such as a cow, a horse, a sheep, a pig, a goat, a dog, or a cat. Included in this definition are pregnant, post-partum, and non-pregnant mammals.

By "symptoms of pre-eclampsia" is meant any of the following: (1) a systolic blood pressure (BP)>140 mmHg and a diastolic BP>90 mmHg after 20 weeks gestation, (2) new onset proteinuria (1+ by dipstik on urinanaysis, >300 mg of protein in a 24 hour urine collection, or random urine protein/creatinine ratio>0.3), and (3) resolution of hypertension and proteinuria by 12 weeks postpartum. The symptoms of pre-eclampsia can also include renal dysfunction and glomerular endotheliosis or hypertrophy. By "symptoms of eclampsia" is meant the development of any of the following symptoms due to pregnancy or the influence of a recent pregnancy: seizures, coma, thrombocytopenia, liver edema, pulmonary edema, and cerebral edema.

By "therapeutic amount" is meant an amount that when administered to a patient suffering from pre-eclampsia or eclampsia is sufficient to cause a qualitative or quantitative reduction in the symptoms of pre-eclampsia or eclampsia as described herein. A "therapeutic amount" can also mean an amount that when administered to a patient suffering from pre-eclampsia or eclampsia is sufficient to cause a reduction in the expression levels of soluble endoglin or sFlt-1 or an increase in the expression levels of VEGF or PlGF as measured by the assays described herein.

By "treating" or "ameliorating" is meant administering a compound or a pharmaceutical composition or administering an ex vivo therapy (e.g., apheresis) to treat or ameliorate a condition or symptom(s) of the condition (e.g., the symptoms of pregnancy related hypertensive disorders described herein). To "treat disease" or use for "therapeutic treatment" refers to administering the treatment to a subject already suffering from a disease to improve the subject's condition. Preferably, the subject is diagnosed with or identified as having a predisposition for developing a pregnancy related hypertensive disorder. As compared with an equivalent untreated control, such amelioration or degree of treatment is an improvement in the condition or symptoms of the treated subject of at least 5%, 10%, 20%, 30%, 40%, 50%, 60%, 70%, 80%, 90%, 95%, 99%, or 100%, as measured by any standard technique.

By "vascular endothelial growth factor (VEGF)" is meant a mammalian growth factor that is homologous to the growth factor defined in U.S. Pat. Nos. 5,332,671; 5,240,848; 5,194,596; and Charnock-Jones et al. (Biol. Reproduction, 48: 1120-1128, 1993), and has VEGF biological activity. VEGF exists as a glycosylated homodimer and includes at least four different alternatively spliced isoforms. The biological activity of native VEGF includes the promotion of selective growth of vascular endothelial cells or umbilical vein endothelial cells and induction of angiogenesis. As used herein, VEGF includes any VEGF family member or isoform (e.g., VEGF-A, VEGF-B, VEGF-C, VEGF-D, VEGF-E, VEGF189, VEGF165, or VEGF 121) or any modified form of VEGF (Tischer et al., *J. Biol. Chem.* 266, 11947-11954, 1991; Neufed et al. *Cancer Metastasis* 15:153-158, 1996), which is described in U.S. Pat. Nos. 6,447,768; 5,219,739; and 5,194,596, hereby incorporated by reference. Although human VEGF is preferred, the invention is not limited to human forms and can include other animal forms of VEGF (e.g. mouse, rat, dog, or chicken).

Other features and advantages of the invention will be apparent from the following description of the preferred embodiments thereof, and from the claims.

DETAILED DESCRIPTION

We have surprisingly discovered that apheresis methods and devices, including those previously known and used to remove positively charged proteins, such as low density lipoproteins or apolipoproteins, from blood can be used to remove sFlt-1 from the blood. Such apheresis methods and devices can be used to treat or ameliorate symptoms of pregnancy related hypertensive disorders.

We have discovered that apheresis methods that were used to remove lipoproteins are effective for the specific removal of sFlt-1 because, while most plasma proteins have isoelectric points between 4 and 6, sFlt1 has an isoelectric point greater than 9.5. Although the apheresis technique may still bind to and remove some LDLs and other positively charged proteins such as fibrinogen, globulin, and C reactive protein, the method will still be selective for sFlt-1, because of its isoelectric point.

Apheresis Methods and Devices

Generally, apheresis includes the removal or withdrawal of blood from the subject's body, removal of one or more components from the blood, and transfusion of the remaining blood back into the subject's body. In the present invention, apheresis is used for the removal, desirably selective removal, of sFlt-1 from the blood of a pregnant woman diagnosed with or suffering from symptoms of a pregnancy related hypertensive disorder.

Apheresis procedures and devices are known in the art and can be used in the present invention. Specifically, the present invention includes the use of apheresis methods and reagents (e.g., negatively charged polymers or polysaccharides) previously used for the removal of positively charged proteins, such as low density lipoprotein, fibrinogen, globulin, and C reactive protein. The apheresis methods of the invention generally utilize a cartridge, column, or filter that include agents, e.g., sulfonated polysaccharides, polystyrene sulfonic acids, or polyacrylic acids that are immobilized with a water-insoluble porous carrier, and that selectively bind to and remove sFlt-1 while leaving other blood components intact. Non-limiting examples of such agents include sulfonated polysaccharide (e.g., hyaluronic acid, chondroitin sulfate, keratin sulfate, heparin sulfate, dextran sulfate), polystyrene sulfonic acid, and polyacrylic acid. Water-insoluble porous carriers include hydrophilic porous carriers which can include porous carriers such as but not limited to polysaccharide (e.g., cellulose, pectin, chitin, agarose, carrageenan, dextran) and hydrophilic polymer (e.g., polyethylene glycol, polyvinyl alcohol, polyacrylic acid, silica gel). All of these molecules have been used in apheresis devices and procedures known in the art for the removal of specific blood proteins, e.g., Low Density Lipoprotein, Lipoprotein(a) (Lp (a)) or the plasma proteins including but not limited to globulin, fibrinogen, and C-reactive protein (CRP). Although heparin-mediated, anionic polyacrylate mediated, and dextran sulfate-mediated-apheresis for the selective removal of sFlt-1 is encompassed within the scope of various embodiments of the invention, dextran sulfate-mediated apheresis is preferred.

As described above, the agent may be immobilized with a water-insoluble porous carrier. For the water-insoluble porous carriers, the average particle diameter when plasma as a cell-free body fluid is used may be 5 to 1,000 μM, preferably 25 to 1,000 μm, most preferably 50 to 300 μm, and in case of the contact of these carriers with blood is 5 to 1,000 μm, and preferably 250 to 1,000 μm, and most preferably 250 to 600 μm. When blood containing citric acid as an anticoagulant is used, the average particle diameter for the water-insoluble porous carrier is 5 to 1,000 μm, and preferably 100 to 600 μm, and most preferably 250 to 300 μm. When blood containing heparin as anticoagulant is used, the average particle diameter for the water insoluble porous carrier is 5 to 1,000 μm, and preferably 250 to 1,000 μm, and most preferably 350 to 600 μm.

Non-limiting examples of such water-insoluble porous carriers include a molecular weight exclusion (i.e., the molecular weight of a molecule having the smallest molecular weight among molecules that cannot enter pores (are excluded) in gel permeation chromatography (Experimental High Performance Liquid Chromatography, edited by Hiroyuki Hatano and Toshihiko Hanai, Kagaku Dojin)) limit of 10,000 to 5,000,000, and preferably 160,000 to 5,000,000, and most preferably 200,000 to 5,000,000. The molecular weight exclusion limit is generally well studied on globular proteins, dextrans, polyethylene glycols, and the like. The carrier used in the present invention suitably employs a value obtained from the globular proteins.

Non-limiting examples of commercially available apheresis columns or devices known in the art for the removal of positively charged lipoproteins include Liposorber® (dextran sulfate-mediated apheresis; Kaneka Pharma); DL75 (Octanova, Kaneka Pharma); H.E.L.P.™ (heparin mediated apheresis; Braun), TheraSorb™ (Miltenyi); and DALI (anionic polyacrylate; Fresenius SE). Although the procedures for apheresis are known in the art and will be known to the skilled artisan, exemplary procedures are provided below.

In one example, once the patient's blood is removed from a vein in the arm, the plasma is separated from the rest of the blood using a membrane plasma filter. The plasma meets the heparin buffer solution or the dextran sulfate buffer solution, at which time a reaction occurs, allowing the sFlt-1 to be removed. The sFlt-1-reduced plasma can then optionally pass through additional filters to remove additional proteins or contaminating materials. The sFlt-1 reduced plasma is then combined with the patient's blood and returned to the patient.

In another example, blood is drawn from the patient's vein and directed to a device that separates plasma from cellular components of the blood. The plasma is then directed into an adsorber. The various adsorbers contain a specific matrix (e.g., heparin, anionic polyacrylate, or dextran sulfate based) that selectively retain the sFlt-1 protein. After passing through the adsorber's matrix, the plasma is recombined with the remaining blood components and returned to the patient.

In yet another example, blood from the patient is circulated extracorporeally using standard apheresis equipment. The blood is separated into the cellular elements (red blood cells, white blood cells and platelets) and fluid (plasma) elements using differential centrifugation or a membrane filter. The plasma is then pumped through the targeted apheresis device where the sFlt-1 will bind to the immobilized heparin or dextran sulfate. The sFlt-1 depleted plasma is then mixed with the cellular blood elements and returned to the patient.

Typically, the apheresis device will be constructed as a cylinder with an inlet to allow plasma to enter at one end, and an outlet at the opposite end to allow the cleaned plasma to exit and be returned to the patient. Other device configurations may also be designed and are within the scope of this invention. The apheresis cartridge may be employed as a single use device or it may be regenerated and used multiple times.

In one example, the apheresis cartridge that has been reduced the capacity during the treatment, is regenerated with eluent include 0.5-25 w/v % inorganic salt solution and as much as 3-10 w/v % saline solution. In desired embodiments, 4-6 w/v % saline solution is used for the regeneration of the apheresis cartridge.

Desirably, the heparin-mediated, anionic polyacrylate-mediated, or dextran sulfate-mediated apheresis will remove at least 10%, 15%, 20%, 25%, 30%, 35%, or 40% of the sFlt-1 in the patient's blood and as much as 45%, 50%, 55%, 60%, 65%, 70%, or 75% of the sFlt-1 in the patient's blood. In desired embodiments, 25% or more, 50% or more, 60% or more, or 75% or more of the sFlt-1 is removed from the patient's blood. In one embodiment, the sFlt-1 is removed such that the subject's sFlt-1 levels return to within 20%, 10%, 5%, 2% or equal to a normal control or reference that is matched for gestational age. Standard assays for sFlt-1 levels are known in the art and can be used to measure the level of the sFlt-1 in the patient's blood before, during, or after apheresis. In one embodiment, the apheresis method results in a clearance of at least 50% of the sFlt-1 protein from the patient's blood as compared to the level before apheresis.

In one embodiment, the pH of the blood is restored to normal biological levels prior to returning to the subject.

The sFlt-1 protein removed in the methods of the invention may be full-length, or an sFlt-1 fragment thereof (e.g., from enzymatic cleavage or degradation), an isoform of sFlt-1 (e.g., alternatively spliced), free, total, or bound sFlt-1.

The apheresis procedures of the invention may be carried out after diagnosis of a pregnancy related hypertensive disorder, e.g., pre-eclampsia or eclampsia, and before or after the onset of clinical symptoms of a pregnancy related hypertensive disorder, e.g., pre-eclampsia or eclampsia. In one embodiment, a patient is identified as being at risk for developing pre-eclampsia and the sFlt-1 levels are measured and monitored. When sFlt-1 levels are increased as compared to normal reference controls, levels, or standard values or curves, the clinician may begin apheresis treatment. Treatment may be given once or repeated until symptoms are diminished; sFlt-1 levels are reduced by at least 10%, 20%, 30%, 40%, 50%, 60%, 70%, 80%, 90%, or more; sFlt-1 levels return to the normal or baseline levels determined early in pregnancy or within 20%, 10%, 5%, or 2% of the normal or baseline levels determined early in pregnancy (e.g., during the first or second trimester); the baby is delivered; the pregnancy is terminated; the subject is deemed to be stable or no longer in need of treatment; or the pregnancy-related hypertensive disorder is fully treated and no longer requires treatment. Other parameters that suggest improvement after apheresis therapy include increasing growth of the fetus, prolonging the pregnancy past 34 weeks of gestation, improvement in hypertension and/or improvement in proteinuria.

In one example, treatment begins in the second trimester. In another example, treatment begins in the third trimester. In another example, treatment begins at 17, 18, 19, 20, 21, 22, 23, 24, 25, 26, 27, 28, 29, 30, 31, 32, 33, 34, 35, 36, 37, 38, 39, or 40 weeks and is continued until no longer necessary.

Combination Therapies

The methods of the present invention may be combined with any other methods for the treatment of a pregnancy related hypertensive disorder (e.g., pre-eclampsia or eclampsia) known in the art or described herein. In one example, the apheresis methods of the present invention are combined with therapeutic methods, in vivo or ex vivo, designed to specifically decrease the sFlt-1 levels (e.g., through the use of an sFlt-1 binding peptide such as VEGF or PlGF or an anti-sFlt-1 antibody) or increase the VEGF or PlGF levels in the subject (see for example, U.S. Pat. Nos. 7,335,362; 7,407,659; and 7,435,419; and PCT Publication Numbers WO 2004/008946 and WO 2005/077007). In another example, the apheresis methods of the present invention are combined with therapeutic methods, in vivo or ex vivo, designed to decrease the level of soluble endoglin (e.g., through the use of an anti-soluble endoglin antibody) or combined with the use of any compound (e.g., polypeptide, small molecule, antibody, nucleic acid, and mimetic) that increases the level or biological activity of TGF-β, eNOS, and PGI$_2$ (see, for example, U.S. Patent Application Publication Numbers 2006/0067937 and 2007/0104707; and PCT Publication Numbers WO 2006/034507; and WO 2008/030283.)

Desirably, the invention features the use of a combination of any one or more of the therapeutic agents described herein. Given our previous discovery that soluble endoglin and sFlt-1 may act in concert to induce vascular damage and pregnancy related hypertensive disorders by interfering with TGF-β1 and VEGF signaling pathway respectively, possibly converging on the NOS signaling pathway, therapeutic methods of the invention include apheresis methods to decrease sFlt-1 levels or activity or increase VEGF or PlGF levels or activity in combination with a compound that decreases soluble endoglin levels or activity or increase TGF-β, NOS, or PGI2 levels or activity. It will be understood by the skilled artisan that any combination of any of the agents can be used for this purpose. For example, an antibody that specifically binds to soluble endoglin can be administered in combination with the apheresis methods of the present invention. In another example, a compound that increases TGF-β1 levels or activity can be administered in combination with the apheresis methods of the present invention in order to target both the endoglin and the sFlt-1 pathway. Alternatively, a combination of the dextran-based (e.g., dextran sulfate) or heparin-based apheresis methods with a targeted apheresis method using antibodies against sFlt-1 or soluble endoglin or both (e.g., using a column that is lined with anti-soluble endoglin or sFlt-1 and circulating the patient's blood through the column) may also be used.

In addition, the apheresis methods of the present may be combined with any methods known to be beneficial during apheresis. In one example, an anti-coagulant therapy is administered to the subject before, during, or after the apheresis. In another example, the subject is given fluid (e.g., saline) for fluid replacement during therapy.

In another embodiment, the invention provides for the use of any chronic hypertension medications used in combination with any of the therapeutic methods described herein. Medications used for the treatment of hypertension during pregnancy include methyldopa, hydralazine hydrochloride, or labetalol. For each of these medications, modes of administration and dosages are determined by the physician and by the manufacturer's instructions.

Monitoring

The apheresis methods of the present invention may be carried out with methods for monitoring the pregnancy related hypertensive condition (e.g., pre-eclampsia or eclampsia) using diagnostic methods known in the art or described herein. Non-limiting examples of diagnostic methods include the measurement and detection of sFlt-1, VEGF, or PlGF as described in U.S. Pat. Nos. 7,335,362; 7,407,659; and 7,435,419; and PCT Publication Numbers WO 2004/008946 and WO 2005/077007. Additional non-limiting examples of diagnostic or monitoring methods that can be used with the apheresis methods of the present invention include the measurement and detection of soluble endoglin, TGF-β1, TGF-β3, activin-A, BMP2, or BMP7 as described in TGF-β1, TGF-β3, activin-A, BMP2, BMP7 as described in U.S. Patent Application Publication Numbers 2006/0067937 and 2007/0104707; and PCT Publication Numbers WO 2006/034507 and WO 2008/030283. Additional non-limiting examples of diagnostic methods include the use of metrics incorporating sFlt-1, PlGF, VEGF, soluble endoglin, or combinations thereof (e.g., sFflt-1/PlGF) as described in U.S. Pat. Nos. 7,335,362; 7,407,659; and 7,435,419; U.S. Patent Application Publication Numbers 2006/0067937 and 2007/0104707; and PCT Publication Numbers WO 2004/008946; WO 2005/077007; WO 2006/034507; and WO 2008/030283.

In one example, apheresis therapy is administered until the blood, plasma, or serum sFlt-1 level is less than 5 ng/ml, desirably less than 2 ng/ml, or until the sFlt-1 levels return to the baseline level determined before onset of pre-eclampsia or eclampsia. In another example, the apheresis therapy can be administered until the serum PlGF level rises to approximately 400 pg/mL or the serum PlGF levels return to baseline level prior to onset of pre-eclampsia or eclampsia. In this embodiment, the levels of soluble endoglin, sFlt-1, PlGF, and VEGF, or any and all of these, are measured repeatedly as a method of not only diagnosing disease but monitoring the treatment and management of the pre-eclampsia and eclampsia.

EXAMPLES

Example 1

Preparation of Adsorbent

In a reaction container, 100 ml of porous cellulose beads (a molecular weight exclusion limit for globular proteins of 5,000,000, a particle diameter of 45 to 105 μm), 100 ml of water, 50 ml of 2N sodium hydroxide, and 17 ml of epichlorohydrin were mixed and reacted at 40° C. for 2 hours. After the reaction, the beads were thoroughly washed with water to give epoxidized cellulose beads. To the obtained epoxidized cellulose beads, 107 ml of 58% aqueous solution of dextran sulfate sodium (a sulfur content of 18%) was added to adjust to pH 9 and the whole was shaken at 45° C. for 22 hours. Then, the gel was filtered off and washed with water. Next, 1.2 ml of monoethanolamine was added to the gel, and the whole was shaken at 45° C. for 2 hours to inactivate unreacted epoxy groups. Then, the product was thoroughly washed with water to give dextran sulfate-immobilized cellulose beads (adsorbent A).

Preparation of Human sFlt-1 Solution

Insect cell recombinant human sFlt-1 (manufactured by RDI) was adjusted to a predetermined concentration with phosphate buffered saline (PBS)/0.1% BSA.

Evaluation of Adsorbent

The dextran sulfate sodium-immobilized cellulose beads were equilibrated with physiological saline. Into a test tube, 0.5 ml of the beads was placed, and excess physiological saline was removed. Into the test tube, 3 ml of human serum containing human sFlt-1 at about 4500 pg/ml was added, the whole was shaken at 37° C. for 2 hours, and then 2.5 ml of supernatant was removed (supernatant A).

To the adsorbent slurry after the treatment, 3 ml of eluent (5% aqueous sodium chloride solution) was added, the whole was shaken at 37° C. for 2 hours, and then 2.5 ml of supernatant was removed (supernatant B).

Separately, 3 ml of human serum containing human sFlt-1 at about 4500 pg/ml was added to 0.5 ml of physiological saline in place of the adsorbent. The whole was shaken at 37° C. for 2 hours to prepare a control solution.

Analytical Method

Using an ELISA kit for measuring human sFlt-1 manufactured by R&D Systems, Inc., the concentration of sFlt-1 was measured in each supernatant prepared in the evaluation process, and from the obtained concentrations of sFlt-1, the adsorption rate and the recovery rate were calculated. The analytical results are shown in Table 1.

The calculation formulae for the adsorption rate and the recovery rate are shown below.

$$\text{Adsorption rate}(\%) = (C_{c1} - C_{a1})/C_{c1} \times 100$$

$$\text{Recovery rate}(\%) = (4 \times C_{a2} - C_{a1})/(3.5 \times (C_{c1} - C_{a1})) \times 100$$

$C_{c1}$: the concentration of sFlt-1 in the control solution
$C_{a1}$: the concentration of sFlt-1 in the supernatant A
$C_{a2}$: the concentration of sFlt-1 in the supernatant B Example 2

Dextran sulfate-immobilized cellulose beads (adsorbent B) were obtained in the same manner as that described in Example 1 except that porous cellulose beads (a molecular weight exclusion limit for globular proteins of 20,000,000, a particle diameter of 45 to 105 μm) were used. Evaluation of the obtained adsorbent B was also carried out in the same manner as that in Example 1.

Example 3

Dextran sulfate-immobilized cellulose beads (adsorbent C) were obtained in the same manner as that described in Example 1 except that porous cellulose beads (an average particle diameter of 195 μm) were used. Evaluation of the obtained adsorbent C was also carried out in the same manner as that in Example 1.

Example 4

Preparation of Adsorbent

First, 100 ml of porous cellulose beads (a molecular weight exclusion limit for globular proteins of 50,000,000, an average particle diameter of about 450 μm), 22 ml of water, 31 ml of 4N aqueous sodium hydroxide solution, and 32 ml of epichlorohydrin were added, and the whole was stirred at 40° C. for 2 hours to be reacted. After the reaction, the beads were thoroughly washed with water to give epoxidized cellulose beads. To 25 ml water, 7.5 g of dextran sulfate (a sulfur content of about 18%) was dissolved to prepare an aqueous dextran sulfate solution, and the solution was added to 50 ml of epoxidized cellulose beads. The mixture was alkalified with an aqueous NaOH solution, and then reacted at 45° C. for 1.5 hours. After the reaction, the beads were thoroughly washed with water and an aqueous sodium chloride solution. Next, a solution of 0.77 g of L-tryptophan dissolved in 50 ml of a diluted aqueous NaOH solution was added and the whole was reacted at 50° C. for 8 hours. Then, the beads were thoroughly washed with water and an aqueous sodium chloride solution to give dextran sulfate and tryptophan-immobilized cellulose beads (adsorbent D). Evaluation of the obtained adsorbent D was carried out in the same manner as that in Example 1.

The analytical results of Examples 1 to 4 using the adsorbents A to D, respectively, are shown in Table 1.

TABLE 1

| Adsorbent | Adsorption rate % | Recovery rate % |
|---|---|---|
| A | 90 | 80 |
| B | 85 | 81 |
| C | 36 | 81 |
| D | 42 | 19 |

Example 5

Extracorporeal Removal of sFlt-1

The calculated isoelectric point for sFlt1 is 9.78. We hypothesized that at a physiological pH of 7.5, sFlt1 protein would be predominantly positively charged. Most plasma proteins have isoelectric points between 4-6 suggesting that at physiological pH they are negatively charged. We therefore hypothesized that an extracorporeal column containing negatively charged material would bind sFlt1 and therefore would be useful to remove sFlt1 in patients with pre-eclampsia. Currently there are a number of commercially available products in the market that are used to remove positively charged apolipoproteins for the treatment of familial homozygous hyperlipidemia (with mutations in the LDL receptor). We performed an ex vivo experiment with discarded human blood (approximately 900 cc of whole blood) spiked with 50 ml of human amniotic fluid containing endogenous sFlt1 at concentrations of approximately 50 ng/ml and performed clearance studies after perfusing the column 3 times as shown below. Pre 0 represents the initial blood concentrations and pre 1, 2, and 3 represent blood concentrations after 1, 2, or 3 rounds of passage through the columns. Data are shown in the table below for 2 different types of dextran sulfate columns (LA 15 and DL75), one anionic polyacrylate column (Dali), and one heparin-based column (Braun). These data demonstrate that dextran sulfate columns are very efficient in removing sFlt1 from human blood. Dextran sulfate columns may be of therapeutic use in patients with pre-eclampsia, particularly those characterized by high circulating sFlt1.

TABLE 2

| | sFlt1 in pg/ml | Clearance % |
|---|---|---|
| Liposorber D DL-75 (Kaneka) | | |
| Pre 0 | 4576 | |
| Pre 1 | 2273 | 50.3 |
| Pre 2 | 1611 | 64.8 |
| Pre 3 | 1185 | 74.1 |
| Liposorber LA 15 (Kaneka) | | |
| Pre 0 | 3791 | |
| Pre 1 | 2225 | 41.3 |
| Pre2 | 1110 | 70.72 |
| Pre 3 | 376 | 90.81 |
| Dali (Fresenius)* | | |
| Pre 0 | 4747 | |
| Pre 1 | 3646 | 23.17 |
| Pre 2 | 1870 | 60.59 |
| Pre 3 | 1574 | 66.84 |
| H.E.L.P (Braun)** | | |
| Pre 0 | 2170 | |
| Pre 1 | 1882 | 13.27 |
| Pre 2 | 1409 | 35.69 |
| Pre 3 | 854 | 60.64 |

*Mini-column with 10 ml of beads coated with anionic polyacrylate.
**Included for comparison.

OTHER EMBODIMENTS

The description of the specific embodiments of the invention is presented for the purposes of illustration. It is not intended to be exhaustive or to limit the scope of the invention to the specific forms described herein. Although the invention has been described with reference to several embodiments, it will be understood by one of ordinary skill in the art that various modifications can be made without departing from the spirit and the scope of the invention, as set forth in the claims. All patents, patent applications, and publications referenced herein are hereby incorporated by reference.

Other embodiments are in the claims.

What is claimed is:

1. A method of treating or ameliorating at least one symptom of a pregnancy related hypertensive disorder in a pregnant subject having elevated soluble Flt-1 (sFlt-1) levels, said method comprising the step of extracorporeally removing sFlt-1 from the pregnant subject, wherein said removing comprises an apheresis procedure, wherein said apheresis procedure comprises the use of dextran sulfate to bind said sFlt-1, wherein said apheresis procedure is sufficient to treat or ameliorate at least one symptom of a pregnancy related hypertensive disorder.

2. A method for reducing the level of sFlt-1 in a bodily fluid of a pregnant subject, said method comprising the step of extracorporeally removing sFlt-1 from the pregnant subject, wherein said removing comprises an apheresis procedure, wherein said apheresis procedure comprises the use of dextran sulfate to bind said sFlt-1, and wherein said apheresis procedure is sufficient to reduce the level of sFlt-1 in a subject in need thereof.

3. The method of claim 1 or 2, wherein the apheresis procedure is repeated at least one time during the pregnancy.

4. The method of claim 1 or 2, wherein the pregnant subject is diagnosed as having a pregnancy related hypertensive disorder.

5. The method of claim 2, wherein the pregnant subject has an increase in the sFlt-1 level or a decrease in the VEGF or PlGF protein levels as compared to a normal reference, standard, or level.

6. The method of claim 1, wherein the pregnant subject has an sFlt-1 level of at least 5 ng/ml.

7. The method of claim 5, wherein the pregnant subject has an sFlt-1 level of at least 5 ng/ml.

8. The method of claim 1, wherein the pregnant subject is at least 17 weeks pregnant.

9. The method of claim 1, wherein the pregnant subject is in the second trimester of pregnancy.

10. The method of claim 1, wherein the pregnant subject is in the third trimester of pregnancy.

11. The method of claim 1, wherein said pregnancy related hypertensive disorder is selected from the group consisting of pre-eclampsia, eclampsia, gestational hypertension, chronic hypertension, HELLP syndrome, and pregnancy with a small for gestational age (SGA) fetus.

12. The method of claim 1 or 2, wherein said apheresis procedure reduces said sFlt-1 levels by at least 20%.

13. The method of claim 5, wherein said apheresis procedure reduces said sFlt-1 levels by at least 20%.

14. The method of claim 1, wherein said method further comprises monitoring said pregnancy related hypertensive disorder in said subject, wherein said monitoring comprises measuring the level of sFlt-1, free VEGF, free PlGF, or soluble endoglin polypeptide in a sample from said subject.

15. The method of claim 14, wherein said monitoring comprises measuring the level of sFlt-1 and PlGF and calculating the ratio of sFlt-1 to PlGF using the ratio sFlt-1/PlGF wherein a decrease in the sFlt-1/PlGF level after said apheresis procedure as compared to a positive reference, standard, or level indicates an improvement in said pregnancy related hypertensive disorder in said subject.

16. The method of claim 14, wherein said monitoring is used to determine if the apheresis procedure should be repeated, wherein a lack of decrease in sFlt-1 or soluble endoglin levels or a lack of increase in free VEGF or free PlGF levels after said apheresis procedure indicates the need for at least one additional apheresis procedure.

17. The method of claim 1, wherein said apheresis procedure is provided until the level of sFlt-1 in said subject is less than 5 ng/ml.

18. The method of claim 1, wherein the method further comprises measuring the levels of sFlt-1 prior to the apheresis procedure and measuring the levels of sFlt-1 during or after said apheresis procedure, wherein the apheresis procedure is administered until the levels of said sFlt-1 polypeptide are reduced by at least 10% during or after said apheresis procedure as compared to said sFlt-1 levels prior to the apheresis procedure.

19. The method of claim 1, wherein said method further comprises the use of an anticoagulation drug compound or an anti-hypertensive drug compound.

20. The method of claim 1, wherein said apheresis procedure further comprising regeneration of said agent with eluent.

21. The method of claim 20, wherein said eluent comprises inorganic salt solution.

22. The method of claim 21, wherein said inorganic salt solution comprises 0.5 to 25 w/v % saline solution.

23. The method of claim 20, wherein said regeneration is performed during a treatment with the apheresis procedure.

24. The method of claim 1, wherein said agent is immobilized with a water-insoluble porous carrier.

25. The method of claim 24, wherein said water-insoluble porous carrier comprises at least one component selected from the group consisting of a polysaccharide, a hydrophilic polymer, cellulose, and polyacrylic acid.

* * * * *